US009885716B2

(12) United States Patent
Lee et al.

(10) Patent No.: US 9,885,716 B2
(45) Date of Patent: Feb. 6, 2018

(54) NANOPROBE AND METHOD FOR DETECTING TARGET ANALYTE USING THE SAME (71) Applicant: SNU R&DB FOUNDATION, Seoul (KR)

(72) Inventors: Yoon-Sik Lee, Anyang-si (KR); Ki Tae Nam, Seoul (KR); Jun ho Chung, Seongnam-si (KR); Dae Hong Jeong, Seoul (KR); Hye Eun Lee, Seoul (KR)

(73) Assignee: SNU R&DB FOUNDATION, Seoul (KR)

(*) Notice: Subject to any disclaimer, the term of this patent is extended or adjusted under 35 U.S.C. 154(b) by 92 days.

(21) Appl. No.: 14/400,797

(22) PCT Filed: May 3, 2013

(86) PCT No.: PCT/KR2013/003857
§ 371 (c)(1),
(2) Date: Nov. 13, 2014

(87) PCT Pub. No.: WO2013/172579
PCT Pub. Date: Nov. 21, 2013

(65) Prior Publication Data
US 2015/0153341 A1 Jun. 4, 2015

(30) Foreign Application Priority Data
May 14, 2012 (KR) .......................... 10-2012-0050851

(51) Int. Cl.
*C07K 14/00* (2006.01)
*A61K 9/50* (2006.01)
*C12Q 1/00* (2006.01)
*C12Q 1/68* (2006.01)
*G01N 33/53* (2006.01)
*G01N 33/569* (2006.01)
*B82Y 15/00* (2011.01)
*G01N 33/543* (2006.01)
*G01N 33/58* (2006.01)
*B82Y 30/00* (2011.01)
*A61K 9/51* (2006.01)
*A61B 8/08* (2006.01)

(52) U.S. Cl.
CPC ........ *G01N 33/56983* (2013.01); *B82Y 15/00* (2013.01); *G01N 33/54373* (2013.01); *G01N 33/56911* (2013.01); *G01N 33/56961* (2013.01); *G01N 33/587* (2013.01); *A61B 8/0808* (2013.01); *A61K 9/5068* (2013.01); *A61K 9/5169* (2013.01); *B82Y 30/00* (2013.01)

(58) Field of Classification Search
CPC .. A61B 8/0808; A61K 9/5068; A61K 9/5169; B82Y 30/00; B82Y 15/00
See application file for complete search history.

(56) References Cited

U.S. PATENT DOCUMENTS

| 7,374,893 | B2* | 5/2008 | Belcher .................... B82Y 5/00 435/4 |
| 7,488,593 | B2 | 2/2009 | Belcher et al. |
| 8,088,982 | B2 | 1/2012 | Belcher et al. |
| 2004/0086897 | A1 | 5/2004 | Mirkin et al. |
| 2008/0266555 | A1 | 10/2008 | Murphy et al. |
| 2011/0092381 | A1* | 4/2011 | Sood ..................... C12Q 1/6816 506/9 |

FOREIGN PATENT DOCUMENTS

| KR | 10-0705755 B1 | 4/2007 |
| KR | 10-0979727 B1 | 8/2010 |
| KR | 10-2010-0102273 A | 9/2010 |
| KR | 10-2010-0107648 A | 10/2010 |
| KR | 20100107648 | * 10/2010 |
| KR | 1020100107648 | * 10/2010 |
| KR | 10-1006700 B1 | 12/2010 |
| KR | 10-1195957 B1 | 10/2012 |

OTHER PUBLICATIONS

Zhao et al., Chem. Sci., 2014, 5:4460-4466.*
He, Shijiang et al., "Graphene-based high-efficiency surface-enhanced Raman scatteringactive platform for sensitive and multiplex DNA detection", Analytical Chemistry, Apr. 24, 2012, vol. 84, No. 10, pp. 4622-4627.
Ki Tae Nam, et al., "Virus-Enabled Synthesis and Assembly of Nanowires for Lithium Ion Battery Electrodes", Science, May 12, 2006, vol. 312 pp. 885-888.
Naomi J. Halas et al., "Plasmons in Strongly Coupled Metallic Nanostructures", Chemical Reviews, 2011, vol. 111, pp. 3913-3961.
Xiangnan Dang et al., "Virus-templated self-assembled single-walled carbon nanotubes for highly efficient electron collection in photovoltaic devices", Nature Nanotechnology,vol. 6. Jun. 2011, pp. 377-354.
Yoon Sung Nam et al., "Biologically templated photocatalytic nanostructures for sustained light water oxidation", Nature Nanotechnology, vol. 5, May 2010, pp. 340-344.
Yu Huang et al.,"Programmable Assembly of Nanoarchitectures Using Genetically Engineered Viruses", NANO Letters, 2005, vol. 5, No. 7, pp. 1429-1434.
Amy Szuchmacher Blum et al.,"Cowpea Mosaic Virus as a Scaffold for 3-D Patterning of Gold Nanoparticles", NANO Letters, 2004, vol. 4, No. 5, pp. 867-870.

(Continued)

*Primary Examiner* — Barry A Chestnut
(74) *Attorney, Agent, or Firm* — STIP Law Group, LLC (57) ABSTRACT Provided is a nanoprobe based on a self-replicating biological material. The nanoprobe includes a binding agent existing in a first region of the biological material and capable of binding specifically to a target analyte, and nanoparticles existing in a second region of the biological material and providing an optical detection signal. The use of the nanoprobe enables quantitative analysis and multiplexed analysis of a target. In addition, the nanoprobe is easy to fabricate on a large scale.

14 Claims, 6 Drawing Sheets (56) References Cited

OTHER PUBLICATIONS

Kenichi Niikura et al.,"Gold Nanoparticle Arrangement on Viral Particles through Carbohydrate Recognition: A Non-Cross-Linking Approach to Optical Virus Detection", Bioconjugate Chem, 2009, vol. 20, pp. 1848-1852.

Kim E. Sapsford et al.,"A cowpea mosaic virus nanoscaffold for multiplexed antibody conjugation: Application as an immunoassay tracer", Biosensors and Bioelectronics, 2006, vol. 21, pp. 1668-1673.

Christine E. Flynn et al. "Viruses as vehicles for growth, organization and assembly of materials", Acta Materialia, 2003, vol. 51, pp. 5687-5880.

Chunyuan Song et al., "Highly sensitive immunoassay based on Raman reporter-labeled immuno-Au aggregates and SERS-active immune substrate", Biosensors and Bioelectronics 25 (2009) pp. 826-831.

Hyunjung Yi et al., "M13 Phage-Functionalized Single-Walled Carbon Nanotubes As Nanoprobes for Second Near-Infrared Window Fluorescence Imaging of Targeted Tumors", NANO Letters, pp. A-H.

Laura Rodriguez-Lorenzoa et al., "Multiplex optical sensing with surface-enhanced Raman scattering: A critical review", Analytics Chimica Acta, 2012, vol. 745, pp. 10-23.

Luca Guerrini et al., "Molecularly-mediated assemblies of plasmonic nanoparticles for Surface-Enhanced Raman Spectroscopy applications", Chem. Soc. Rev., 2012, vol. 41, pp. 7085-7107.

Debadyuti Ghosh et al., "M13-templated magnetic nanoparticles for targeted in vivo imaging of prostate cancer", Nature Nanotechnology, Published Online: Sep. 16, 2012 | DOI: 10.1038/NNAN0.2012.146.

Yunqing Wang et al.,"SERS Tags: Novel Optical Nanoprobes for Bioanalysis" Chem. Rev. 2013, vol. 113, pp. 1391-1428.

Laura Fabris et al.,"Aptatag-Based Multiplexed Assay for Protein Detection by Surface-Enhanced Raman Spectroscopy", small, 2010, vol. 6, No. 14, pp. 1550-1557.

Yuwei Pei et al., "Highly sensitive SERS-based immunoassay with simultaneous utilization of self-assembled substrates of gold nanostars and aggregates of gold nanostars", J. Mater. Chem. B, 2013, vol. 1, pp. 3992-3998.

Zachary M. Carrico et al.,"N-Terminal Labeling of Filamentous Phage to Create Cancer Marker Imaging Agents", ACSNANO, 2012, vol. 6, No. 8, pp. 6675-6680.

Sebastian Schlucker. "SERS Microscopy: Nanoparticle Probes and Biomedical Applications", ChemPhysChem, 2009, vol. 10, pp. 1344-1354.

Kai Li et al.,"Chemical Modification of M13 Bacteriophage and Its Application in Cancer Cell Imaging", Bioconjugate Chem. 2010, vol. 21, pp. 1369-1377.

Laura Fabris et al.,"SERS Aptatags: New Responsive Metallic Nanostructures for Heterogeneous Protein Detection by Surface Enhanced Raman Spectroscopy", Adv. Funct. Mater. 2008. vol. 18, pp. 2518-2525.

Radha Narayanan et al.,"Cetyltrimethylammonium Bromide-Modified Spherical and Cube-Like Gold Nanoparticles as Extrinsic Raman Labels in Surface-Enhanced Raman Spectroscopy Based Heterogeneous Immunoassays", Analytical Chemistry, Mar. 15, 2008, vol. 80, No. 6, pp. 2265-2271.

Youjin Lee et al.,"Virus-templated Au and Au—Pt core—shell nanowires and their electrocatalytic activities for fuel cell applications", Energy Environ. Sci., 2012, vol. 5, pp. 8328-8334.

Seung-Wuk Lee et al., "Ordering of Quantum Dots Using Genetically Engineered Viruses", Science, May 3, 2002, vol. 296, pp. 892-895.

Chuanbin Mao et al.,"Virus-Based Toolkit for the Directed Synthesis of Magnetic and Semiconducting Nanowires", Science, vol. 303, Jan. 9, 2004, pp. 213-217.

Gonçalo Doria et al., "Noble Metal Nanoparticies for Biosensing Applications", Sensors, 2012, vol. 12, pp. 1657-1687.

Amy M. Wen et al., Photonics and plasmonics go viral: self-assembly of hierarchical metamaterials, Rend. Fis. Acc. Lincei (2015) 26 (Suppl 2):S129-S141.

* cited by examiner

$$\text{Enhancement Factor} = \frac{I_{SERS}/N_{SERS}}{I_N/N_N}$$

$I_{SERS}$ : Intensity of SERS probe
$I_N$ : Intensity of bulk
$N_{SERS}$ : Number of molecules in SERS probe
$N_N$ : Number of molecules in bulk Measured enhancement factors(EF) at 1563cm$^{-1}$

Average EF = 1.32E+06

[FIG. 8]

NANOPROBE AND METHOD FOR DETECTING TARGET ANALYTE USING THE SAME

CROSS REFERENCE TO PRIOR APPLICATIONS

This application is a National Stage Application of PCT International Patent Application No. PCT/KR2013/003857 filed on May 3, 2013, under 35 U.S.C. § 371, which claims priority to Korean Patent Application No. 10-2012-0050851 filed on May 14, 2012, which are all hereby incorporated by reference in their entirety.

TECHNICAL FIELD

The present invention relates to a nanoprobe and a method for detecting a target analyte using the same. More specifically, the present invention relates to a novel nanoprobe that is suitable for use in quantitative multiplexed analysis and is easy to fabricate on a large scale, and a method for detecting a target analyte using the nanoprobe.

BACKGROUND ART

Disease biomarkers are markers that can detect qualitative and quantitative changes in structure or concentration to diagnose diseases. Excess disease biomarkers are present in blood as a result of leakage of proteins from tissues, which is involved in the development of a disease. Accurate detection of the disease biomarkers is crucial to diagnose the disease. Recent research efforts have been directed towards the development of disease diagnostic technology through comprehensive verification of some proteins or peptides closely related to corresponding diseases rather than single biomarkers. Under these circumstances, there is a need for diagnostic technologies based on disease biomarkers suitable for quantitative multiplexed analysis.

For multiplexed analysis, nanoprobes should generate different signals without any interference between the signals and should respond sensitively to target analytes. Generally, fluorescent molecules bound to nanoprobes have been used for signal detection in quantitative measurements based on antigen-antibody reactions. However, there is a limitation in multiplexed analysis using different fluorescent molecules because broad peaks appear in the spectra of the fluorescent molecules. The type of laser light should be changed depending on the kind of substance and the problems of photobleaching and blinking may arise. Photobleaching refers to a phenomenon in which signals get weaker with the passage of time.

On the other hand, molecules have inherent Raman signals whose spectral widths are very narrow. Accordingly, labeling of target-specific binding agents with different kinds of Raman markers enables multiplexed analysis of the targets and allows the molecules to be simultaneously excited under single light irradiation, enabling rapid detection of the targets using simple measuring systems. However, there is a difficulty in detecting target analytes due to very low intensity of Raman signals. This difficulty is overcome by the use of metal nanoparticles that can increase the intensity of Raman signals, ideally by up to 14 orders of magnitude, to provide sufficient signal intensity for measurement. Numerous studies have focused on the fabrication of nanoprobes using metal nanoparticles to enhance Raman signals, thus being suitable for various applications (Cao, Y. W. C., Jin, R. C., Mirkin, C. A.: Nanoparticles with Raman spectroscopic fingerprints for DNA and RNA detection. *Science* 2002, 297 (5586): 1536-1540; Nie, S. M., Emery, S. R.: Probing single molecules and single nanoparticles by surface-enhanced Raman scattering. *Science* 1997, 275 (5303): 1102-1106; Li, J. F., Huang, Y. F., Ding, Y., Yang, Z. L., Li, S. B., Zhou, X. S., Fan, F. R., Zhang, W., Zhou, Z. Y., Wu, D. Y. et al.: Shell-isolated nanoparticle-enhanced Raman spectroscopy. *Nature* 2010, 464 (7287): 392-395; Kneipp, K., Kneipp, H., Itzkan, I., Dasari, R. R., Feld, M. S.: Ultrasensitive chemical analysis by Raman spectroscopy. *Chem Rev* 1999, 99 (10): 2957-2976; Kim, J. H., Kim, J. S., Choi, H., Lee, S. M., Jun, B. H., Yu, K. N., Kuk, E., Kim, Y. K., Jeong, D. H., Cho, M. H. et al.: Nanoparticle probes with surface enhanced Raman spectroscopic tags for cellular cancer targeting. *Anal Chem* 2006, 78 (19): 6967-6973; Qian, X. M., Peng, X. H., Ansari, D. O., Yin-Goen, Q., Chen, G. Z., Shin, D. M., Yang, L., Young, A. N., Wang, M. D., Nie, S. M.: In vivo tumor targeting and spectroscopic detection with surface-enhanced Raman nanoparticle tags. *Nature Biotechnology* 2008, 26 (1): 83-90). However, there have been some limitations in the fabrication of nanoprobes. First, sufficiently enhanced Raman signals are, in practice, difficult to obtain, unlike theoretical values. Second, signals are not uniformly increased. Third, attachment of binding agents specific to target analytes to metal nanoparticles for biomarker detection lacks directivity, making it difficult to quantitatively analyze the target analytes.

DETAILED DESCRIPTION OF THE INVENTION

According to one aspect of the present invention, there is provided a nanoprobe based on a self-replicating biological material, including a binding agent existing in a first region of the biological material and capable of binding specifically to a target analyte, and nanoparticles existing in a second region of the biological material and providing an optical detection signal.

According to a further aspect of the present invention, there is provided a nanoprobe based on a self-replicating biological material, including a binding agent existing in a first region of the biological material and capable of binding specifically to a target analyte, and nanoparticles existing in a second region of the biological material and enhancing a Raman signal, wherein the binding agent is expressed by modification of a protein in the first region and the alignment of the nanoparticles is controlled by modification of a protein in the second region.

According to another aspect of the present invention, there is provided a method for detecting a target analyte using a nanoprobe, including modifying a first region of a self-replicating biological material to express a binding agent, attaching nanoparticles to a second region of the biological material to enhance a Raman signal, fixing a Raman reporter to the nanoparticles to fabricate a nanoprobe, binding a target analyte to the binding agent of the nanoprobe to form a complex, and analyzing the complex by surface-enhanced Raman spectroscopy.

MODE FOR CARRYING OUT THE INVENTION

Embodiments of the present invention will now be described in detail with reference to the accompanying drawings. These embodiments are provided so that this disclosure is thorough, and will fully convey the scope of the invention to those skilled in the art. Accordingly, the present invention may be embodied in many different forms and should not be construed as limited to the exemplary embodiments set forth herein. In the drawings, the dimensions, such as widths, lengths and thicknesses, of elements may be exaggerated for clarity. The same reference numerals denote the same elements throughout the drawings. The drawings are explained from an observer's point of view. It will be understood that when an element is referred to as being "on" another element, it can be directly on the other element, or one or more intervening elements may also be present therebetween.

One embodiment of the present invention provides a nanoprobe based on a self-replicating biological material. As used herein, the term "probe" refers to a material that is capable of binding specifically to a target analyte to be detected in a sample. This binding is specifically indicative of the presence of the target analyte in the sample. As used herein, the term "sample" is intended to include tissue, cell, whole blood, serum, plasma, saliva, phlegm, cerebrospinal fluid and urine samples containing target analytes to be detected, but is not limited thereto. As used herein, the term "target analyte" refers to a material to be detected that is present in the sample. The target analyte is not limited and may be any of those known in the art. The target analyte is preferably a peptide nucleic acid (PNA), a locked nucleic acid (LNA), a peptide, a polypeptide, a protein, RNA, or DNA. More specifically, suitable target analytes include those derived from organisms, analogs thereof, and those produced ex vivo, for example, enzymes, proteins, microorganisms, animal and plant cells and organs, neurons, DNAs, and RNAs. Examples of the DNAs include cDNAs, genomic DNAs, and oligonucleotides. Examples of the RNAs include genomic RNAs, mRNAs, and oligonucleotides. Examples of the proteins include antibodies, antigens, enzymes, and peptides.

When a sample containing a target analyte is brought into contact with the nanoprobe, the target analyte in the sample specifically binds to the nanoprobe. When the target is a PNA, LNA, RNA or DNA, specific hybridization occurs between complementary sequences. When the target is a protein, a complex-forming reaction may occur simply through direct binding of the nanoprobe to the sample protein or binding reactions may occur between the nanoprobe and the sample protein, including transformation or modification of the nanoprobe by enzymatic activity of the sample protein. Therefore, binding reactions between the target protein and the nanoprobe molecules may include binding reactions between proteins and biomolecules, such as antigen-antibody reactions and ligand-receptor reactions, and substrate-enzyme reactions between proteins and biomolecules.

Figure 1:
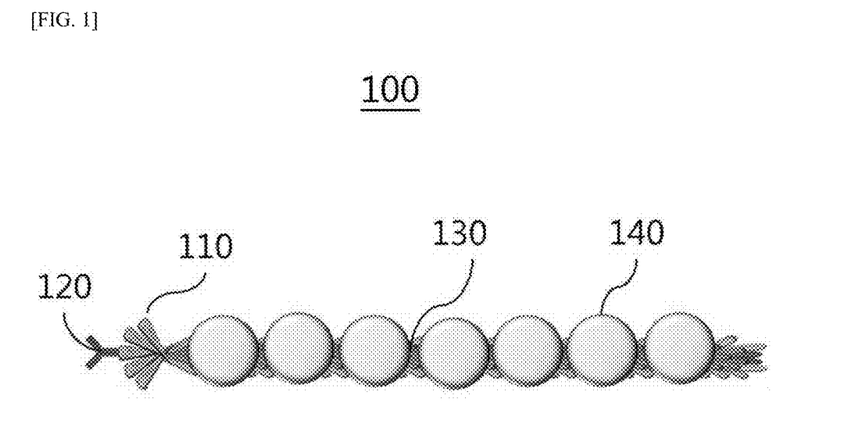
FIG. 1 is a diagram showing an exemplary nanoprobe based on a self-replicating replicating biological material.

FIG. 1 is a diagram showing an exemplary nanoprobe based on a self-replicating biological material. Referring to FIG. 1, the nanoprobe 100 includes a binding agent 120 existing in a first region 110 of the biological material and nanoparticles 140 existing in a second region 130 of the biological material.

The biological material may be surface modified by genetic engineering or chemical processing. The surface-modified biological material is used as a support of the nanoprobe 100. The biological material may be selected from the group consisting of viruses, bacteria, and yeasts. Examples of the viruses include, but are not particularly limited to, M13, TMV, T7, and CTX. For example, the biological material may be a rod-like helical virus. Examples of the bacteria include, but are not particularly limited to, *Bacteroides, Clostridium, Streptococcus, Staphylococcus, Pseudomonas, Haemophilus, Legionella, Mycobacterium, Escherichia, Salmonella, Shigella*, and *Listeria* species.

The first region 110 may include a specified protein structure and may be genetically engineered or chemically processed to express the binding agent 120.

The binding agent 120 may be a substance that binds specifically to a target analyte, such as an antigen, a nucleic acid, a protein, a peptide or a tumor marker. For example, the binding agent 120 may be an antibody capable of binding specifically to an antigen.

The binding agent 120 is conjugated to the first region 110. This conjugation allows for alignment of reactive sites of the binding agent 120 with the target analyte in a particular direction. That is, the binding agent 120 may have a defined orientation so as to facilitate specific binding to the target analyte.

Since the number of a specific kind of protein molecules present in the first region 110 of each biological material is constant, the number of binding agents per nanoprobe can be controlled within a limited range depending on the dimensions of the first region 110. Therefore, quantitative analysis is enabled due to the constant number and the same direction of the binding agents 120 in all nanoprobes 110.

The second region 130 may exist at a location different from the first region 110 on the surface of the biological material and may include a specific protein structure. The protein structure of the second region 130 may be modified to facilitate attachment of the nanoparticles 140. In one embodiment of the present invention, the alignment conditions of the nanoparticles 140, for example, the gaps between the nanoparticles 140 and the number of the nanoparticles 140, may be controlled by genetic engineering or chemical processing of the second region 130.

The nanoparticles 140 provide a specific optical detection signal, which enables application of the biological material to the nanoprobe. The optical detection signal may be selected from the group consisting of fluorescence, Raman scattering, graphics, optical patterns, and combinations thereof.

The nanoparticles 140 may be, for example, organic or inorganic particles containing a fluorescent material. Alternatively, the nanoparticles 140 may be semiconductor nanoparticles or metal nanoparticles to which Raman reporter molecules are attached. The nanoparticles 140 may be surface modified with a suitable ligand to facilitate binding to the second region 130. The ligand may include a functional group for covalent or noncovalent bonding with a functional group present in the second region 130. The functional group of the ligand may be, for example, an amine, carboxyl or hydroxyl group.

In one embodiment of the present invention, the optical detection signal may be Raman scattering light. In this case, the nanoparticles 140 may be metal nanoparticles such as gold, silver, palladium, aluminum or copper nanoparticles, oxide nanoparticles, or semiconductor nanoparticles. The metal, oxide or semiconductor nanoparticles are introduced into the second region 130 so that a Raman signal from Raman reporter molecules attached to the nanoparticles 140 can be greatly enhanced by the phenomenon of surface-enhanced Raman scattering (SERS). There is no particular restriction on the kind of the Raman reporter molecules. For example, the Raman reporter may be selected from the group consisting of 4,4'-dipyridyl (DP), Crystal Violet (CV), 4-mercaptotoluene (4-MT), 3,5-dimethylbenzenethiol (3,5-DMT), thiophenol (TP), 4-aminothiophenol (4-ATP), benzenethiol (BT), 4-bromobenzenethiol (4-BBT), 2-bromobenzenethiol (2-BBT), 4-isopropylbenzenethiol (4-IBT), 2-naphthalenethiol (2-NT), 3,4-dichlorobenzenethiol (3,4-DCT), 3,5-dichlorobenzenethiol (3,5-DCT), 4-chlorobenzenethiol (4-CBT), 2-chlorobenzenethiol (2-CBT), 2-fluorobenzenethiol (2-FBT), 4-fluorobenzenethiol (4-FBT), 4-methoxybenzenethiol (4-MOBT), 3,4-dimethoxybenzenethiol (3,4-DMOBT), 2-mercaptopyrimidine (2-MPY), 2-mercapto-1-methylimidazole (2-MMI), 2-mercapto-5-methylbenzimidazole (2-MBI), 2-amino-4-(trifluoromethyl) benzenethiol (2-ATFT), benzyl mercaptan (BZMT), benzyl disulfide (BZDSF), 2-amino-4-chlorobenzenethiol (2-ACBT), 3-mercaptobenzoic acid (3-MBA), 1-phenyltetrazole-5-thiol (1-PTET), 5-phenyl-1,2,3-triazole-3-thiol (5-PTRT), 2-iodoaniline (2-IAN), phenyl isothiocyanate (PITC), 4-nitrophenyl disulfide (4-NPDSF), 4-azido-2-bromoacetophenone (ABAPN), and mixtures thereof. Any aromatic compound including a thiol, azido, cyano, isocyano or thioisocyano group may also be used as the Raman reporter.

There is no particular restriction on the shape of the nanoparticles 140. The nanoparticles 140 may be selected from the group consisting of spherical particles, strawberry or sea urchin-like spherical particles on which variously shaped nanoparticles are placed, anisotropic particles, hollow particles, asymmetric particles, edged particles, and mixtures thereof. The nanoparticles 140 may be, for example, nanospheres, nanorods, or nanocubes. The nanoparticles 140 may have other geometric and non-geometric shapes. Particularly, the anisotropic particles, such as rod-like, triangular, prismatic, and cubic particles, and the edged particles can provide enhanced Raman scattering signals compared to spherical particles. The size as well as shape of the nanoparticles 140 can be appropriately controlled to create as many surface plasmons as possible. The nanoparticles 140 having the above-described shapes can be produced by many methods reported in the literature.

According to the present invention, the nanoprobe 100 may be provided in plurality. Even in this case, the nanoprobes 100 may use biological materials, each of which has a first region 110 and a second region 130 whose dimensions are defined. The dimensions of the biological materials are substantially the same. With these dimensions, the numbers of the binding agents 120 and the nanoparticles 140 in the nanoprobes 100 can be controlled at constant levels depending on the dimensions of the regions 110 and 130, respectively, and can be maintained constant without any substantial difference between the nanoprobes 100.

In a preferred embodiment of the present invention, M13 virus may be used as the biological material. The M13 virus is approximately 6.5 nm in diameter and 880 nm in length and has a structure consisting of different proteins at different locations. There are 5 proteins VII (pVII) and 5 protein IX (pIX) at one end of the virus and proteins III (pIII) and VI (pVI), each consisting of 5 molecules, at the other end of the virus. The middle portion of the virus body consists of about 2700 copies of a major protein VIII (pVIII).

In the case where the nanoprobe 100 uses M13 virus as the biological material, the first region 110 may include pIII and the second region 130 may include pVIII. In this case, the binding agent 120 may be expressed on the pIII and the nanoparticles 140 may be attached to the pVIII. The Raman reporter molecules may be fixed to the nanoparticles 140 and, if needed, a ligand may be introduced on the surface of the nanoparticles 140 to facilitate binding of the nanoparticles 140 to the second region 130 including pVIII. Depending on the amino acid sequence expressed in the second region 130 by a suitable technique such as genetic engineering, the gaps between the nanoparticles 140 and the alignment density of the nanoparticles 140 can be controlled.

Alignment of the metal nanoparticles in the single nanoprobe 100 allows for a greatly enhanced Raman signal, enabling multiplexed analysis of target analytes using the Raman signal. As another approach to amplify a Raman signal, the use of edged metal nanoparticles may be considered. A fixed number of the previously formed nanoparticles can be attached to the biological material at uniform intervals, making the probe uniform.

In addition, the ability of the biological material to self-replicate enables the fabrication of nanoprobes 100 with the same characteristics on a large scale.

Figure 2:
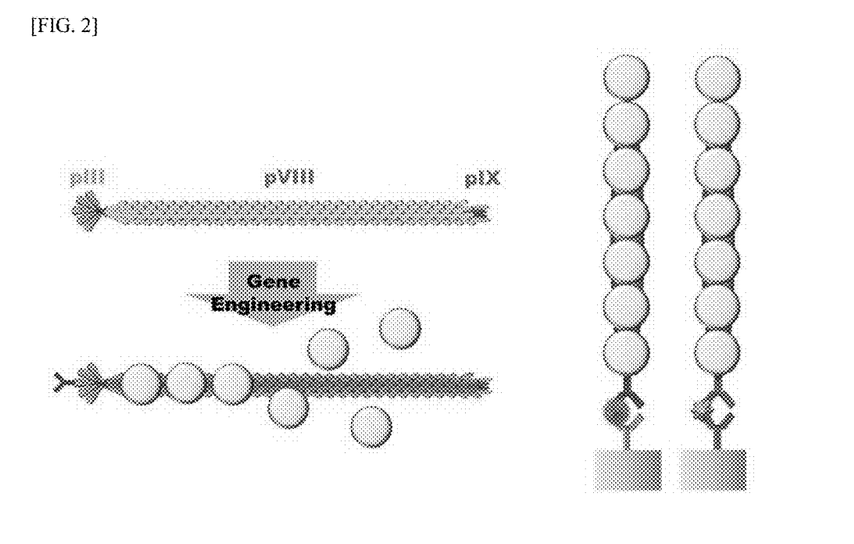
FIG. 2 is a schematic diagram showing a process for fabricating nanoprobes using genetically modified M13 virus.

FIG. 2 is a schematic diagram showing a process for fabricating nanoprobes using genetically modified M13 virus. Referring to FIG. 2, binding agents and nanoparticles may be introduced on the surface of M13 virus. In this case, the virus may be genetically engineered to express the same or different peptide sequences on the various kinds of proteins. For example, the pVIII portion of the M13 virus may be used to amplify a Raman signal, and at the same time, an antibody may be expressed on the pIII portion for biomarker detection.

A specific amino acid sequence is expressed on the pVIII portion of the genetically modified virus for attachment of the nanoparticles to the virus, ensuring uniform alignment of the nanoparticles along the shape of the virus. The fixed length of the pVIII portion defines the number of the nanoparticles that can be attached to the virus, ensuring generation of a uniform signal. Specifically shaped nanoparticles known to have the ability to significantly amplify signals can be aligned on the virus to fabricate Raman probes that have a higher degree of amplification of Raman signals and are more uniform than conventional Raman probes.

The pIII portion where an antibody appears is a feature that can be provided only by a virus structure. The nanoprobe of the present invention is distinguished from previous nanoprobes in that an antibody can be expressed on the virus structure, avoiding the need to additionally attach an antibody to the virus structure. Therefore, antibodies are aligned in a particular direction and the number thereof can be controlled within a limited range, thereby providing a quantifiable system. That is, conjugation of antibodies on the pIII portion may allow the antibodies to have a defined orientation such that the antibodies easily and specifically bind to antigens. This conjugation can effectively function to substantially bind almost all antibodies on the nanoprobe to corresponding antigens. On the other hand, the M13 virus has five proteins III at one end thereof. Modification of the fixed number of proteins present in the virus enables the expression of a constant number of antibodies. For example, genetic engineering may modulate the expression of antibodies (binding agents), ideally a maximum of 5 antibodies per nanoprobe. Results of an actual antibody expression experiment on M13 virus revealed that genetic engineering resulted in a mixture of M13 virus in which antibodies were expressed and wild-type M13 virus in which antibodies were not expressed and the number of antibodies expressed for each virus was generally from 0 to 3, mainly 1. The average number of antibodies expressed for M13 virus may be determined depending on the kind of the antibodies or experimental conditions for genetic engineering. If an average of one antibody is expressed on each nanoprobe, it can be considered that only one antigen (target analyte) is detected in one nanoprobe, i.e. the ratio of the number of nanoprobes to the number of antigens is 1:1. Therefore, the amount of antigens can be quantified by measuring the amount of nanoprobes.

Figure 3:
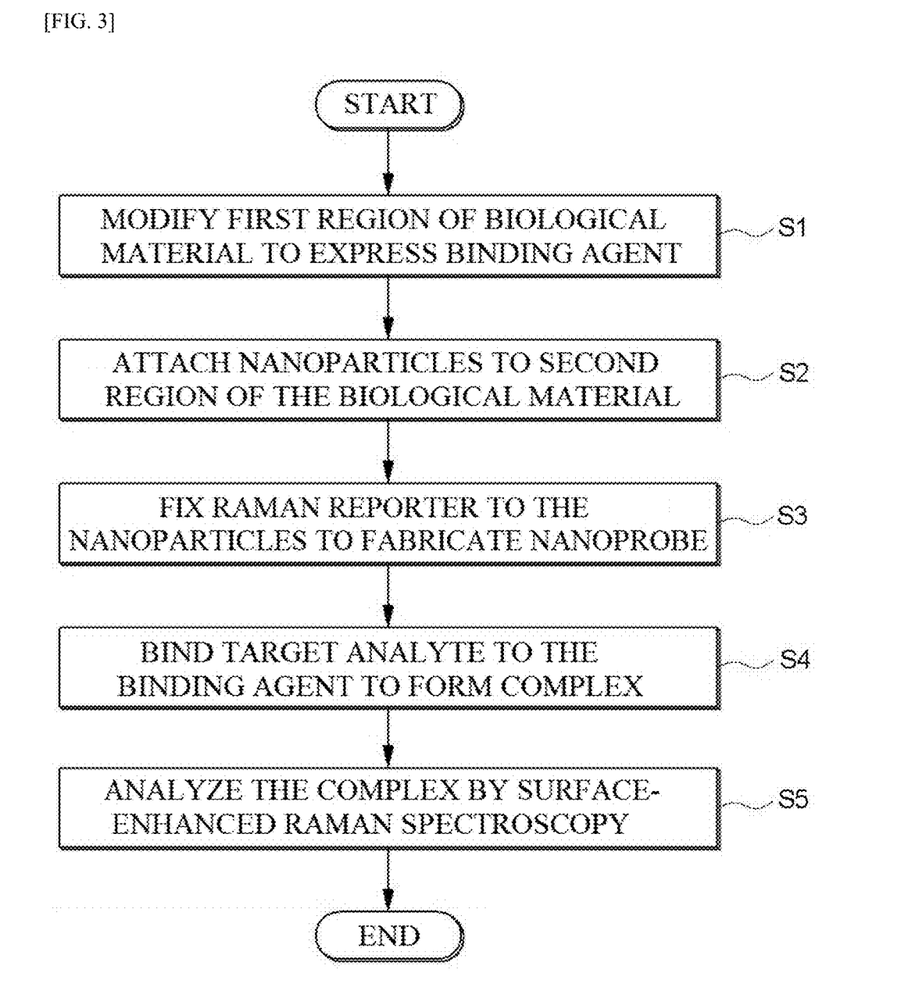
FIG. 3 is a flow chart illustrating an exemplary method for detecting a target analyte.

One embodiment of the present invention provides a method for detecting a target analyte using a biological material-based nanoprobe. FIG. 3 is a flow chart illustrating an exemplary method for detecting a target analyte. Referring to FIG. 3, in step S1, a first region of a self-replicating biological material is modified to express a binding agent. In step 2, nanoparticles are attached to a second region of the biological material to enhance a Raman signal. In step 3, a Raman reporter is fixed to the nanoparticles. In step S4, a target analyte is allowed to bind to the binding agent to form a complex. In step S5, the complex is analyzed by surface-enhanced Raman spectroscopy. The target analyte can be quantified by measuring the amount of the nanoprobe in the complex through the Raman signal.

In some embodiments, the nanoparticles used in step S2 are preferably edged metal nanoparticles that have excellent optical properties and intense electromagnetic field enhancement. If needed, the second region may be modified or a ligand may be introduced on the surface of the nanoparticles to ensure uniform attachment of the nanoparticles to the second region.

Figure 4:
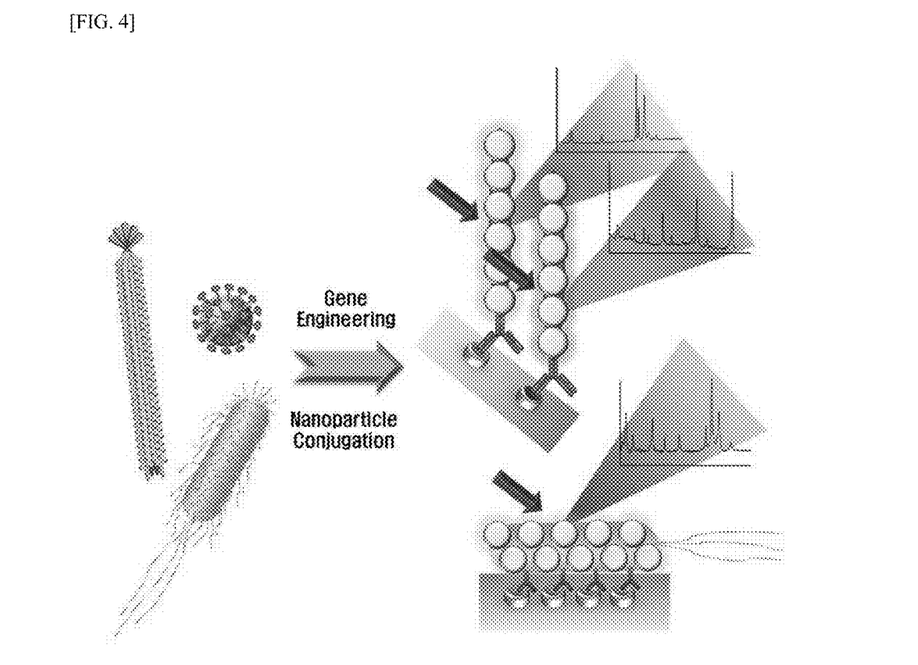
FIG. 4 is a schematic diagram showing a process for analyzing target analytes by surface-enhanced Raman spectroscopy using nanoprobes based on various biological materials.

FIG. 4 is a schematic diagram showing a process for analyzing target analytes by surface-enhanced Raman spectroscopy using nanoprobes based on various biological materials.

Figure 5:
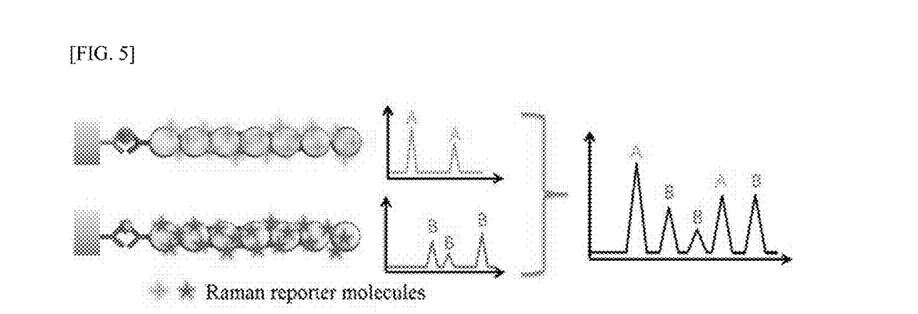
FIG. 5 is a conceptual diagram showing multiplexed quantitative analysis of several kinds of targets through one-time SERS mapping.

FIG. 5 is a conceptual diagram showing multiplexed quantitative analysis of several kinds of targets through one-time SERS mapping. Virus-based nanoprobes (hereinafter, referred to as "virus probes") according to one embodiment of the present invention are labeled with their inherent SERS signals. One or two antibodies are attached to each probe. Each probe with one or two antibodies corresponds to several micrometers in size. For example, if the virus probes are bound to target analytes in a tissue sample, the locations of the probes in the map are discerned by the SERS signals. The number of the targets is proportional to the number of the virus probes and the kind of the target analytes can be distinguished by the kind of the labeled SERS signals of the virus probes. Accordingly, multiplexed quantitative analysis of various kinds of targets can be performed through one-time SERS mapping.

Figure 6:
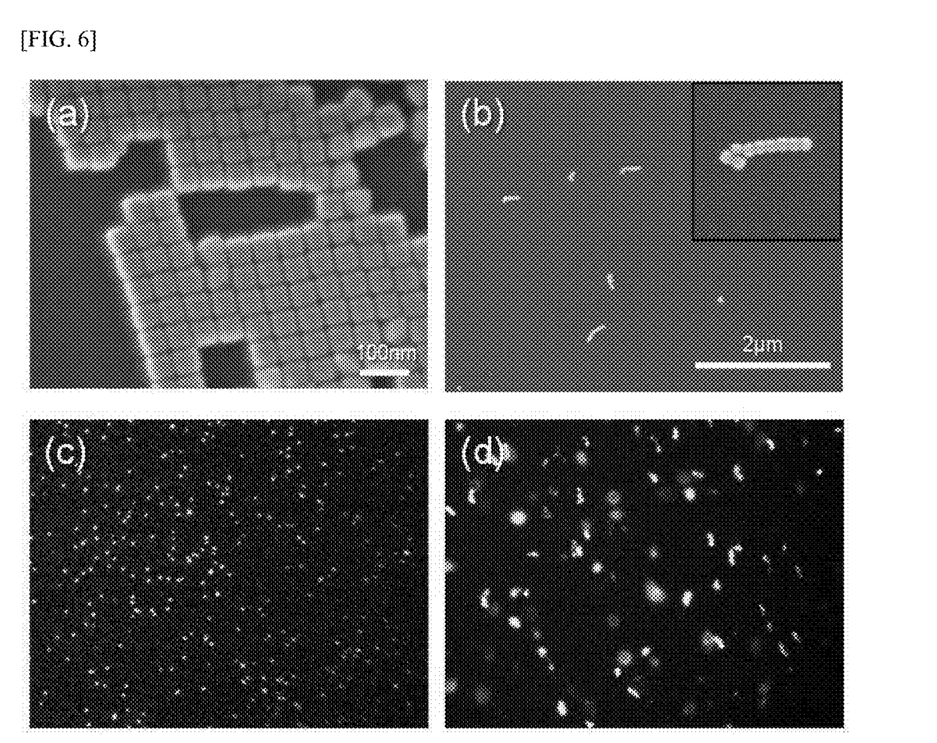
FIG. 6 shows (a) a SEM image of synthesized gold nanocubes, (b) a SEM image of gold nanocube-bound virus probes, (c) a dark-field (DF) microscopy image of synthesized gold nanocubes, and (d) a DF microscopy image of gold nanocube-bound virus probes.

FIG. 6 shows SEM images of synthesized gold nanocubes and fabricated virus probes. Referring to the SEM images of FIG. 6, 50-nm gold nanocubes were uniformly well synthesized and uniformly attached and aligned in lines on a virus. DF scattering images show that the gold nanocubes were uniformly synthesized and colored green in the solutions. When mixed with the virus, the nanoparticles aggregated, and as a result, red-shifted yellow spots were observed in the DF scattering image.

Figure 7:
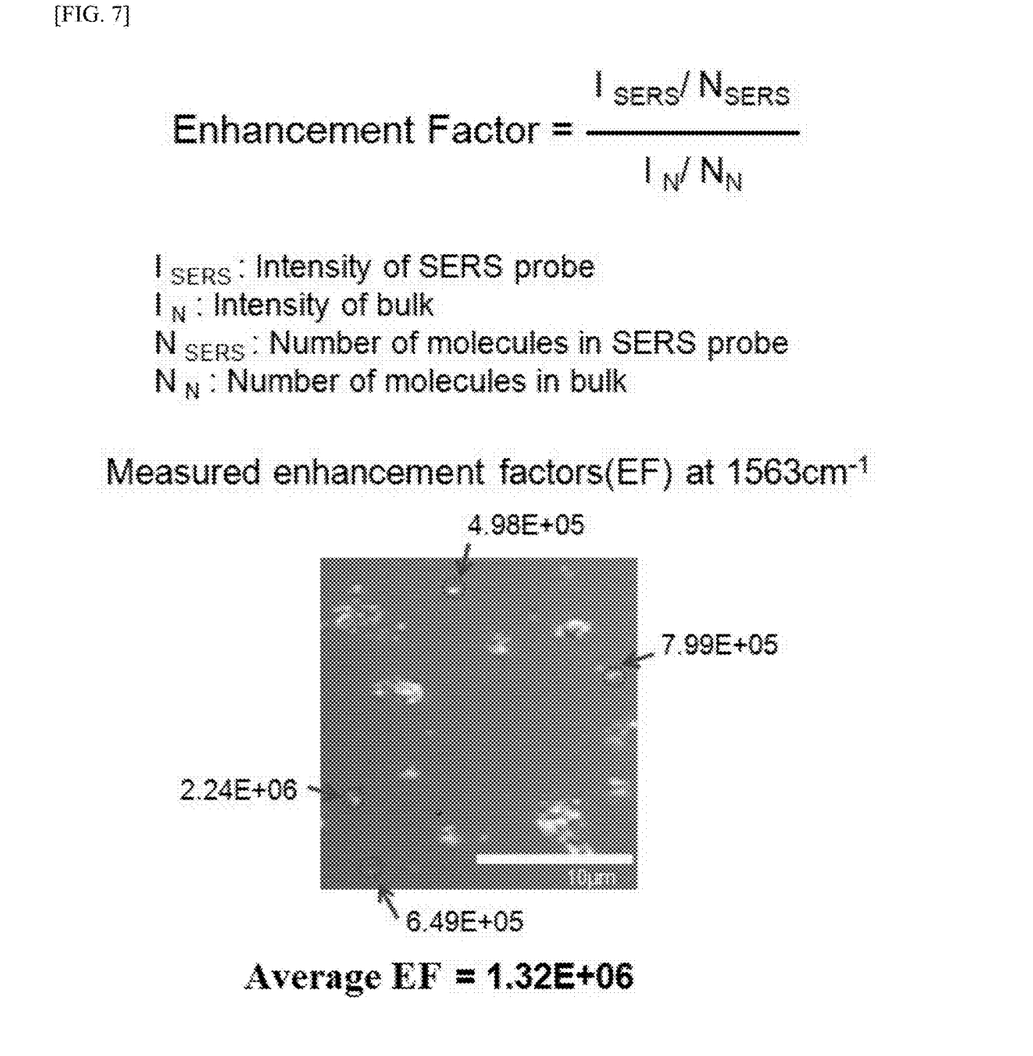
FIG. 7 shows a formula for calculating the SERS enhancement factor of a synthesized virus probe and shows enhancement factors of probes at different locations and an average value thereof.

FIG. 7 shows quantitative data showing increments in the Raman signal of fabricated virus probes. Referring to FIG. 7, the intensity of a Raman signal from one Raman chemical was compared with the increased intensity of a Raman signal from the virus probe to which the Raman chemical was attached. The results of comparison show how much one molecule increased the Raman signal in the virus probe. This increment was calculated and defined as an "enhancement factor". The enhancement factors of the virus probes at the locations appeared in the optical images amplified the signals were calculated to investigate how much the virus probes amplified the signals. The enhancement factors were averaged, and as a result, the signals were increased by a factor of about $10^6$.

Figure 8:
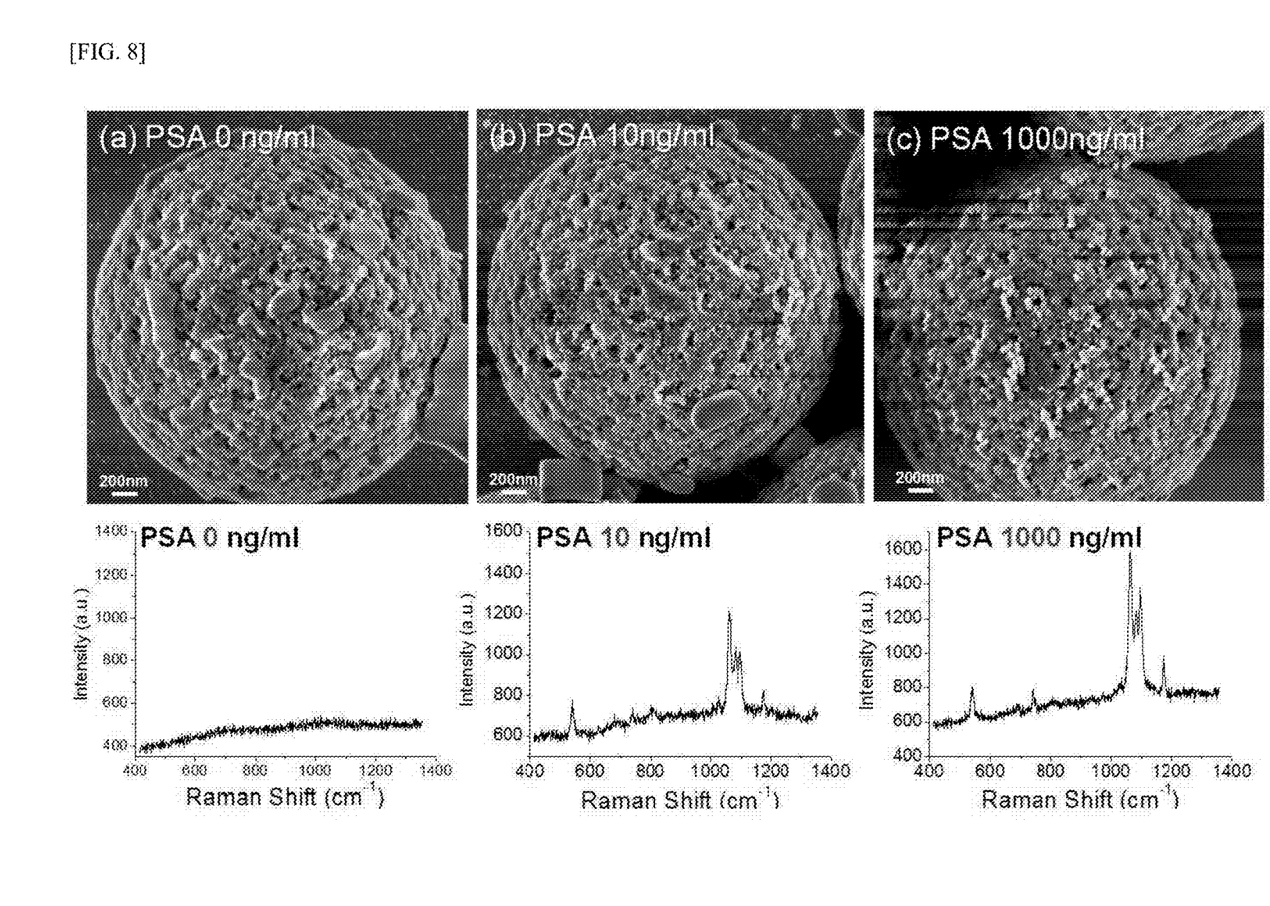
FIG. 8 shows SEM images and Raman spectra of magnetic bead-captured virus probes for various concentrations of prostate specific antigen (PSA) (0 ng/ml (a), 10 ng/ml (b), and 1000 ng/ml (c)), which was detected by the virus probes. The virus probes are represented in yellow.

The virus probes were assayed at different antigen concentrations. The results are shown in FIG. 8. Referring to FIG. 8, no cubes were observed on the surfaces of the probes in the absence of PSA, but virus probes including aligned cubes were observed at PSA concentrations of 10 ng/ml and 1000 ng/ml. As the number of the virus probes increased, the intensity of Raman signals increased.

As described above, the nanoprobe of the present invention can be uniformly fabricated on a large scale because it is based on a self-replicating biological material. The biological material can be genetically engineered or chemically processed to form functional groups at selected locations thereof. This modification allows the binding agent or the nanoparticles to be easily introduced into the desired sites of the biological material. The nanoprobe of the present invention enables quantitative analysis and multiplexed analysis for disease diagnosis. The binding agent specific to a target analyte exists as an element in the biological material of the nanoprobe to quantitatively analyze the target analyte. That is, the expression of the binding agent is controlled using the specific region of the biological material so that the target analyte can be quantified by measuring the amount of the probe. In addition, the plasmon-generating nanoparticles can be uniformly attached to and aligned on the biological material to uniformly amplify a Raman signal having very narrow spectral widths, enabling multiplexed analysis.

The present invention will be explained in more detail with reference to the following examples. These examples are provided for illustrative purposes only and it will be obvious to those skilled in the art that they are not intended to limit the scope of the present invention in accordance with the subject matter of the present invention.

EXAMPLES

Example 1: Viral Genetic Engineering

Gene VIII (gVIII) existing on a wild-type M13 bacteriophage vector was engineered to attach nanoparticles to a second region of the biological material. The bacteriophage vector was genetically engineered to introduce a peptide sequence having the ability to bind to the nanoparticles into the N-terminus of pVIII, a surface protein of the M13 bacteriophage.

First, the recognition sequence of KpnI, a restriction enzyme that has not existed in the wild-type M13 bacteriophage vector, was introduced by the following procedure. Polymerase chain reaction was performed on oligonucleotide 2 (5'-GAA AGA CAG CAT CGG TAC CAG GGT AGC AAC GGC TAC-3') upstream of the recognition sequence of SnaBI, a restriction enzyme existing on the bacteriophage vector, and oligonucleotide 1 (5'-TGT TTC GCG CTT GGT ATA ATC G-3') obtained by replacing the original sequence on the vector (CTCGTT) with the recognition sequence of KpnI (CTGGTA). Polymerase chain reaction was performed on oligonucleotide 3 (5'-GTA GCC GTT GCT ACC CTG GTA CCG ATG CTG TCT TTC-3') having a sequence complementary to that of the oligonucleotide 2 and oligonucleotide 4 (5'-CAA ACG AAT GGA TCC TCA TTA AAG-3') including the recognition sequence of BamHI, a restriction enzyme existing on the bacteriophage vector. The resulting products were attached to each other by polymerase chain reaction of the oligonucleotides 1 and 4. This product and the wild-type M13 bacteriophage vector were treated with restriction enzymes SnaBI and BamHI and were allowed to react at 37° C. for DNA cleavage. The two kinds of cleaved DNAs were mixed and a ligase was added thereto to ligate the vector with the gene including the KpnI recognition sequence, completing the construction of a modified M13 bacteriophage vector.

Second, a sequence having the ability to bind to gold nanoparticles was inserted into the modified M13 bacteriophage vector by the following procedure. Polymerase chain reaction was performed on oligonucleotide 5 (5'-cggggtac-cgatgctgtetttcgctgctgaggtgageggcagcagcccggatagcgatcccg-caaaagcg-3') including the recognition sequence of the restriction enzyme KpnI and a gold nanoparticle-binding sequence and the oligonucleotide 4 to insert the gold nanoparticle-binding sequence between amino acids Ala-Glu and Gly-Asp located at the N-terminus of pVIII. Restriction enzymes KpnI and BamHI were added to this product and the modified M13 bacteriophage vector, respectively, followed by reaction at 37° C. for DNA cleavage. The two kinds of cleaved DNAs were mixed and ligated together by the addition of a ligase to construct a new M13 bacteriophage vector in which the gold nanoparticle-binding sequence was inserted.

The gold nanoparticle-binding sequence was expressed in a second region of the biological material by the following procedure. E. coli ER2738 was transformed with the vector constructed above, followed by culture in Super Broth (37° C., 250 rpm, 16 h, supplemented with kanamycin). The culture solution was centrifuged (3,000 rpm, 15 min) and the supernatant was heated at 70° C. for 20 min. After centrifugation (3,000 rpm, 15 min), the supernatant was collected.

To express a binding agent in a first region of the biological material, a binding agent-labeling gene was inserted into the 5'-end of gIII existing on phage plasmid pComb3XSS by the following procedure. The recognition sequence of restriction enzyme SfiI was included in both forward and reverse oligonucleotides for amplification of the binding agent-labeling gene, followed by polymerase chain reaction. To this product and the phage plasmid pComb3XSS was added the restriction enzyme SfiI, followed by reaction at 50° C. for DNA cleavage. The two kinds of cleaved DNAs were mixed and ligated together by the addition of a ligase to construct phage plasmid Comb3X in which the binding agent was inserted.

A bacteriophage expressing the binding agent in the first region of the biological material and the gold nanoparticle-binding agent in the second region of the biological material was constructed by the following procedure. The phage plasmid pComb3X including the binding agent was introduced into E. coli ER2738 via transformation, followed by culture in Super Broth (37° C., 250 rpm, supplemented with ampicillin). The culture solution was found to have an absorbance of 0.8-1.0 at 600 nm. To the culture solution was added $10^{11}$/ml bacteriophage expressing the gold nanoparticle-binding sequence in the second region. Culture was continued (37° C., 250 rpm, 16 h, supplemented with kanamycin). The culture solution was centrifuged (3,000 rpm, 10 min) to collect the supernatant in which bacteria were precipitated. The supernatant was found to contain a bacteriophage expressing the binding agent in the first region and the gold nanoparticle-binding sequence in the second region.

Example 2: Production of Gold Nanocubes

Gold nanocubes were produced based on the method described in Small, 4, 2059 (2008). The shape of the gold nanocubes was controlled using cetyltrimethylammonium bromide (CTAB) as a ligand, which is relatively well attached to the crystal plane (100) of the nanocubes. First, $HAuCl_4$ was reduced by $NaBH_4$ to form very small crystals. The crystals were allowed to slowly grow in a growth solution to synthesize gold nanocubes.

Specifically, 7.5 ml of 0.1 M CTAB was mixed with 0.25 ml of 0.01 M $HAuCl_4$ and 0.8 ml of 0.01 M $NaBH_4$ was added thereto to obtain very small (2-3 nm sized) crystals. 5 µl of the crystals were diluted with water and allowed to slowly grow in a growth solution. The growth solution was prepared by mixing 8.0 ml of pure water, 1.6 ml of CTAB, 0.2 ml of $HAuCl_4$, and 0.95 ml of L-ascorbic acid. The resulting gold nanocubes were collected by centrifugation and washed twice with water to remove excess reagents.

Example 3: Binding of the Gold Nanoparticles to Virus

A virus was mixed with a dispersion of the gold nanocubes in water. The mixture was left for 1 h.

Example 4: Fixing of Raman Reporter

4-Chlorothiophenol (4-CBT) was used as a Raman reporter. The gold nanocubes were mixed with $10^{-6}$ M 4-CBT. After standing the mixture for 30 min, the Raman reporter was adsorbed to the gold surfaces.

Example 5: Dark Field and Raman Measurements

Dark-field (DF) scattering images and spectra were measured to easily determine whether the gold nanocubes were attached to the virus. The unbound gold nanocubes were colored green and showed a peak in the surface plasmon resonance (SPR) scattering band between 500 and 550 nm. When the gold nanocubes were bound to the virus, the color changed from yellow to red and the peak moved toward a longer wavelength by plasmonic coupling between the nanoparticles.

FIG. 6 shows (c) a DF scattering image of the gold nanocubes and (d) a DF scattering image of the gold nanocube-bound virus. A change in color and aggregation were observed, demonstrating that of the gold nanocubes were attached to the virus.

Example 6: Enhancement Factor Calculation

To evaluate the performance of the virus probes as SERS probes, a calculation was made to determine how much the Raman signals were increased in the CBT molecules adsorbed to the virus probes. The virus probes were immobilized on glass and the Raman signals were measured at different locations. The Raman signal from each virus probe ($I_{SERS}$) was divided by the number of the CBT molecules ($N_{SERS}$) adsorbed to the virus probe to obtain a Raman signal intensity ($I_{SERS}/N_{SERS}$) from one molecule in the virus probe. In the same manner as above, the Raman signal from one CBT molecule ($I_N/N_N$) was calculated. The Raman signal intensity ($I_{SERS}/N_{SERS}$) from one molecule in the virus probe was divided by the Raman signal from one CBT molecule ($I_N/N_N$) to know how much one CBT molecule adsorbed to the virus probe increased the signal. As a result, the signals were increased on average by a factor of about $10^6$.

Example 7: Measurement of Amount of Antigen Using Magnetic Beads

Magnetic beads were used to confirm the ability of the virus probes to detect an antigen. The magnetic beads can be easily attached to various functional groups of proteins via epoxide groups present on the surface thereof. Capture antibodies were immobilized on the magnetic beads via 24-h aging. PSA was used as the antigen. PSA was stirred for 2 h in the magnetic beads to which the capture antibodies have been attached. After stirring, samples were prepared in which PSA at different concentrations was attached to the magnetic beads. When the virus probes were placed in the magnetic beads to which the antigen has been attached, the amount of the probes attached to the magnetic beads varied depending on the antigen concentration because the PSA-capturing antibodies were expressed on the pIII portion of the virus. The results can also be confirmed from the SEM images of FIG. 8. No gold nanocubes were observed in the absence of PSA but the amount of the gold nanocubes increased with gradually increasing PSA concentration. This increase in the amount of the gold nanocubes generated enhanced Raman signals, whose intensities can be confirmed in the Raman spectra corresponding to the respective concentrations (FIG. 8).

The invention claimed is:

1. A nanoprobe based on a self-replicating biological material, comprising:
   a binding agent existing in a first region of the biological material and capable of binding specifically to a target analyte; and
   nanoparticles existing in a second region of the biological material and providing an optical detection signal,
   wherein the first and the second regions are not overlapped on a surface of the biological material, and
   wherein the biological material is M13 virus, the first region of the M13 virus comprises protein III (pIII), and the second region of the M13 virus comprises protein VIII (pVIII).

2. The nanoprobe according to claim 1, wherein the biological material is selected from the group consisting of viruses, bacteria, and yeasts.

3. The nanoprobe according to claim 1, wherein the binding agent has a defined orientation so as to facilitate specific binding to the target analyte.

4. The nanoprobe according to claim 1, wherein the binding agent is provided in plurality and the number of the binding agents in the nanoprobe is controlled within a limited range depending on the dimensions of the first region.

5. The nanoprobe according to claim 1, wherein the first region is genetically engineered or chemically processed to express the binding agent.

6. The nanoprobe according to claim 1, wherein the second region is genetically engineered or chemically processed to control the arrangement of the nanoparticles.

7. The nanoprobe according to claim 1, wherein the optical detection signal is selected from the group consisting of fluorescence, Raman scattering, graphics, optical patterns, and combinations thereof.

8. The nanoprobe according to claim 1, wherein the nanoparticles are selected from the group consisting of spherical particles, strawberry or sea urchin-like spherical particles on which variously shaped nanoparticles are placed, anisotropic particles, hollow particles, asymmetric particles, edged particles, and mixtures thereof.

9. The nanoprobe according to claim 1, wherein the number of the nanoparticles is controlled at a constant level depending on the dimensions of the second region.

10. A nanoprobe based on a self-replicating biological material, comprising:
    a binding agent existing in a first region of the biological material and capable of binding specifically to a target analyte; and
    nanoparticles existing in a second region of the biological material and enhancing a Raman signal,
    wherein the binding agent is expressed by modification of a protein in the first region and is provided in plurality and the number of the binding agents in the nanoprobe is controlled within a limited range depending on the dimensions of the first region, and the alignment of the nanoparticles is controlled by modification of a protein in the second region,
    wherein the first and the second regions are not overlapped on a surface of the biological material, and
    wherein the biological material is M13 virus, the first region comprises protein III (pIII), and the second region comprises protein VIII (pVIII).

11. The nanoprobe according to claim 10, wherein Raman reporter molecules are fixed to the nanoparticles.

12. The nanoprobe according to claim 10, wherein a ligand is introduced on the surface of the nanoparticles to facilitate binding of the nanoparticles to the second region.

13. The nanoprobe according to claim 10, wherein the gaps between the nanoparticles and the alignment density of the nanoparticles are controlled depending on the amino acid sequence expressed in the second region.

14. The nanoprobe according to claim 10, wherein the nanoparticles are selected from the group consisting of spherical particles, strawberry or sea urchin-like spherical particles on which variously shaped nanoparticles are placed, anisotropic particles, hollow particles, asymmetric particles, edged particles, and mixtures thereof.

* * * * *